United States Patent [19]

Thornton

[11] Patent Number: 5,038,991
[45] Date of Patent: Aug. 13, 1991

[54] SURGICAL STAPLER

[75] Inventor: Curtis W. Thornton, Cary, N.C.

[73] Assignee: Edward Weck Incorporated, Princeton, N.J.

[21] Appl. No.: 454,805

[22] Filed: Dec. 21, 1989

[51] Int. Cl.⁵ ............................................. A61B 17/00
[52] U.S. Cl. .................................................. 227/19
[58] Field of Search ........................ 227/19, 120, 121

[56] References Cited

U.S. PATENT DOCUMENTS

| | | | |
|---|---|---|---|
| 4,043,504 | 8/1977 | Hueil et al. | 227/19 X |
| 4,591,086 | 5/1986 | Campbell et al. | 227/19 |
| 4,662,555 | 5/1987 | Thornton et al. | 227/120 X |
| 4,887,756 | 12/1989 | Puchy | 227/19 |

*Primary Examiner*—Timothy V. Eley
*Attorney, Agent, or Firm*—Robert E. Lee; Gene Warzecha

[57] ABSTRACT

A surgical stapler, preferably in a single use disposable form, comprises a combination of a staple feeding mechanism and a staple forming mechanism secured in a frame and an actuating trigger functionally connected to both the stable feeding mechanism and the staple forming mechanism, wherein the staple feeding mechanism includes a rail to guide contained staples serially to a staple forming position and a shuttle in association with the rail as a movable staple retaining cover, the shuttle being functionally connected to the trigger for movement in the same direction and the same time as the staples. The rail includes a pair of spaced apart flexible members which support the next staple to be deformed but which flex to move out of the staple path at the onset of deformation. The staple after formation is positioned between the members so that there is no interference between the rail and the deformed staple.

4 Claims, 5 Drawing Sheets

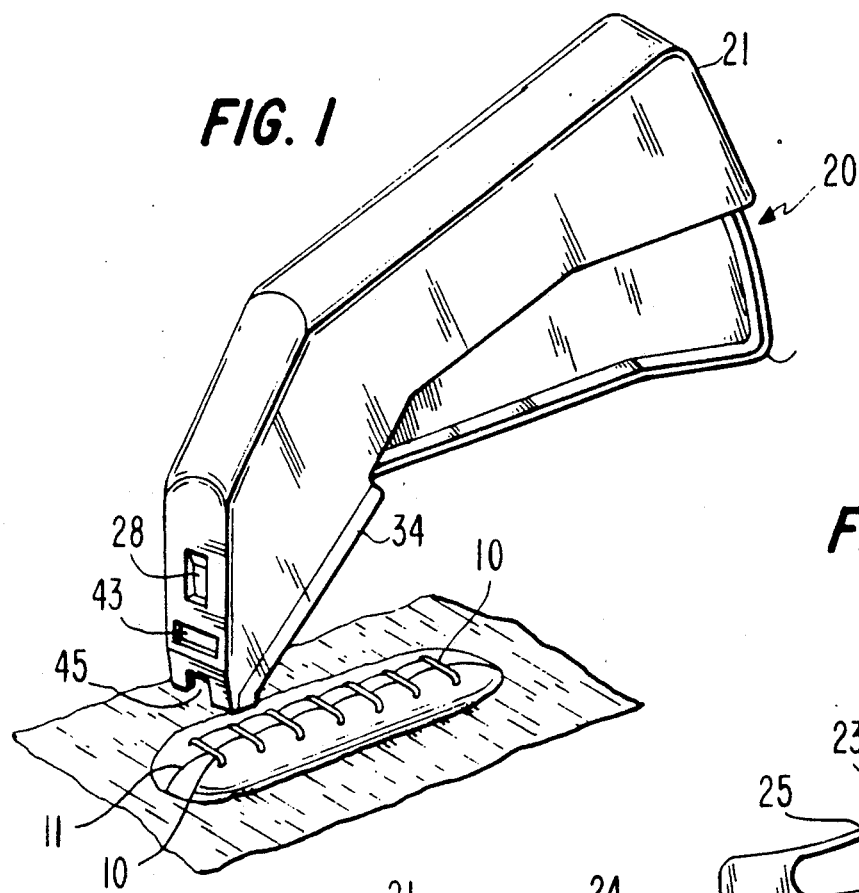
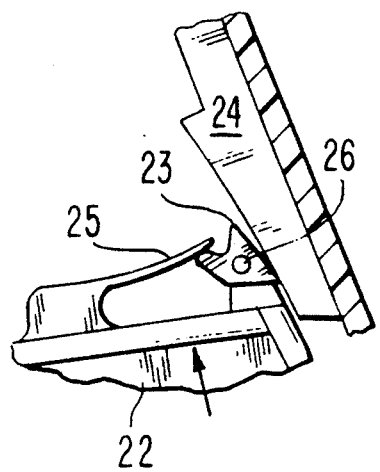
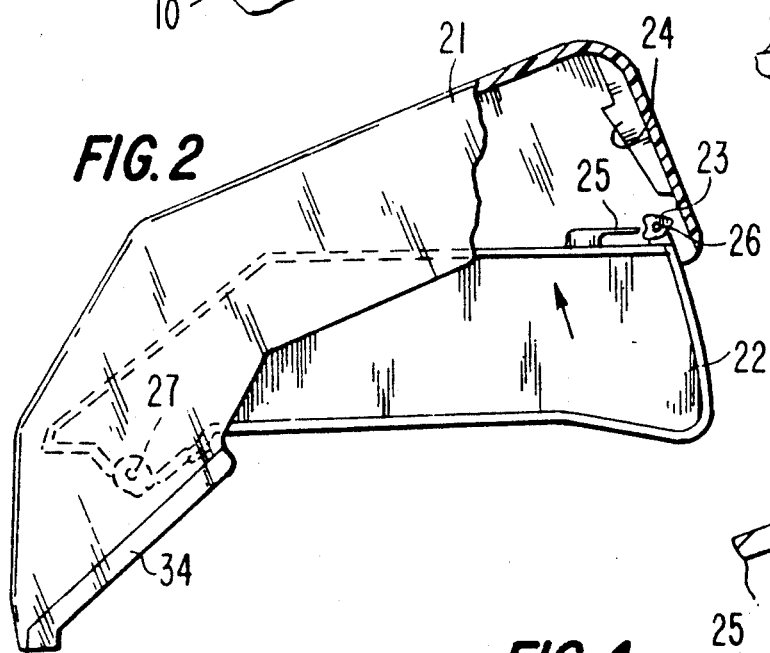
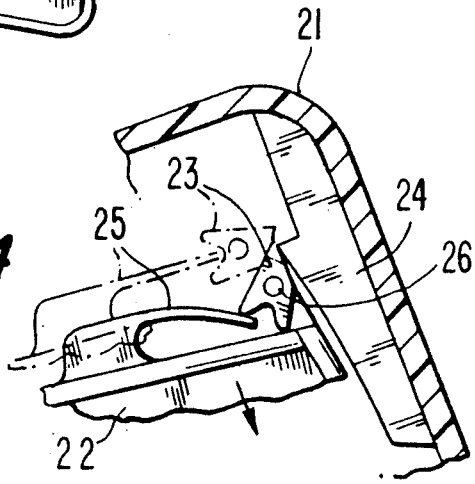

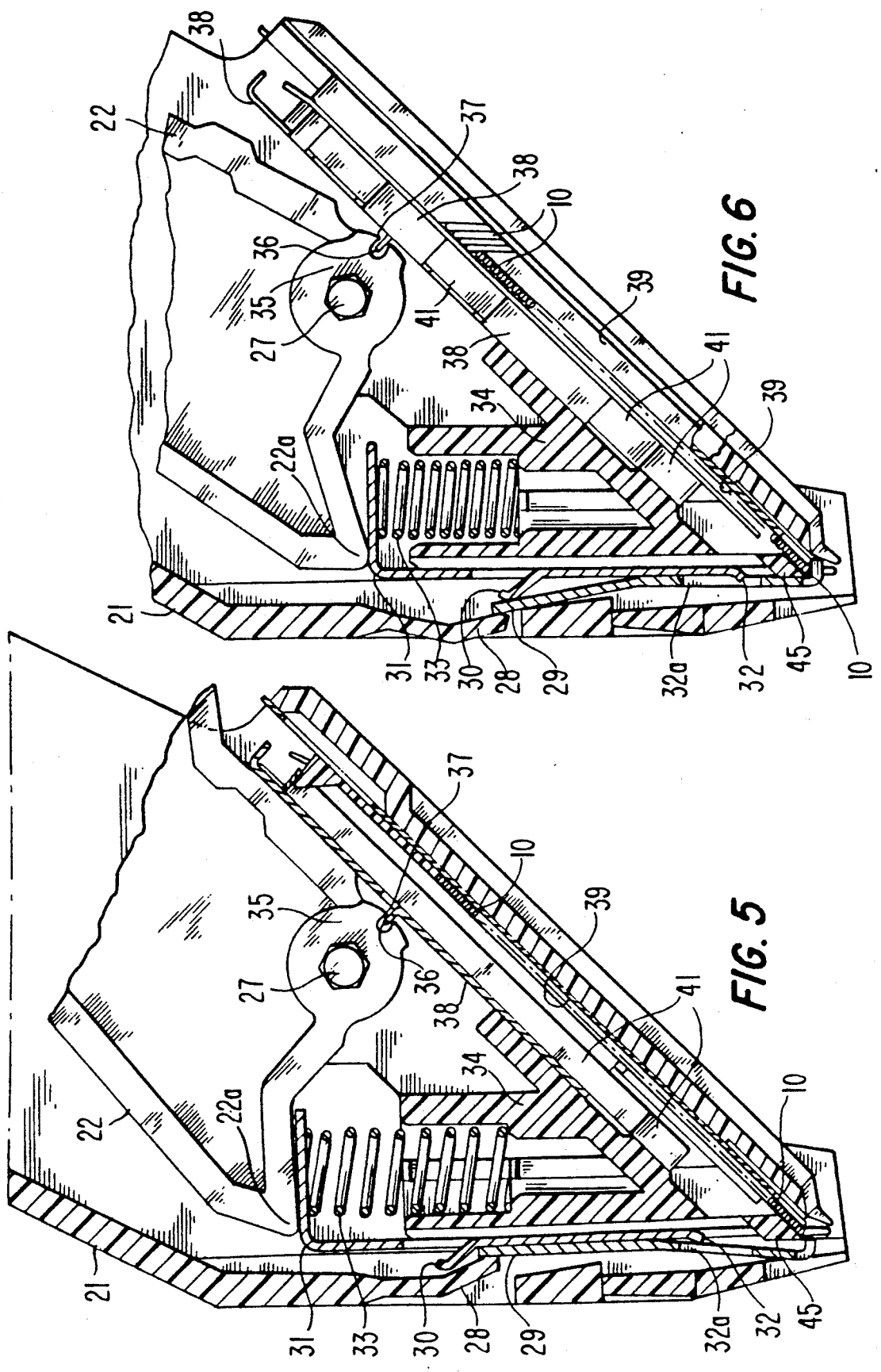

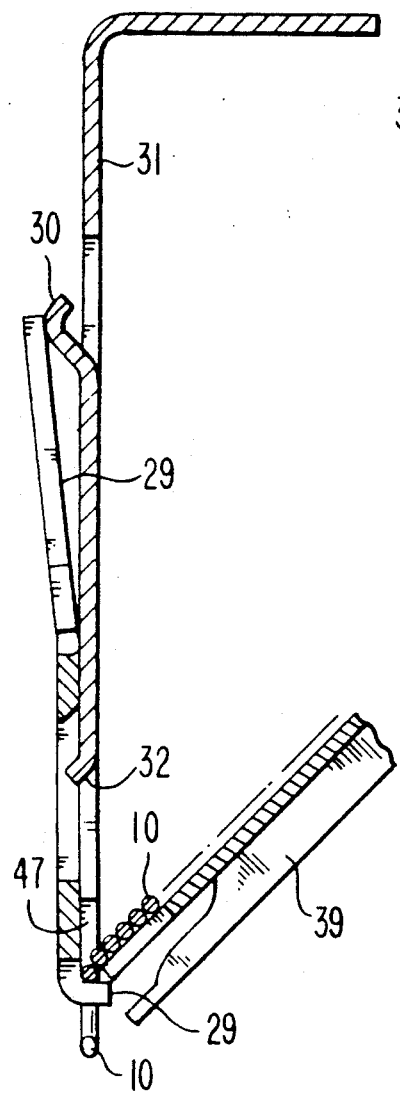
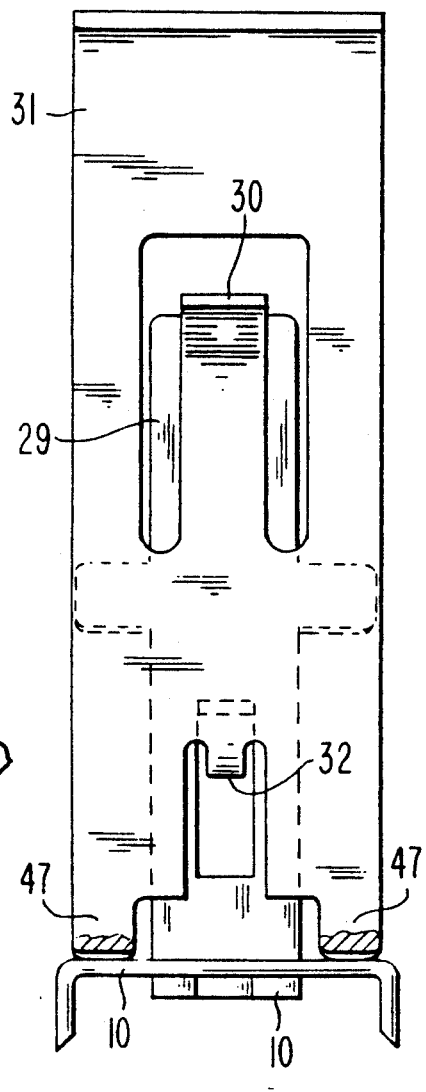
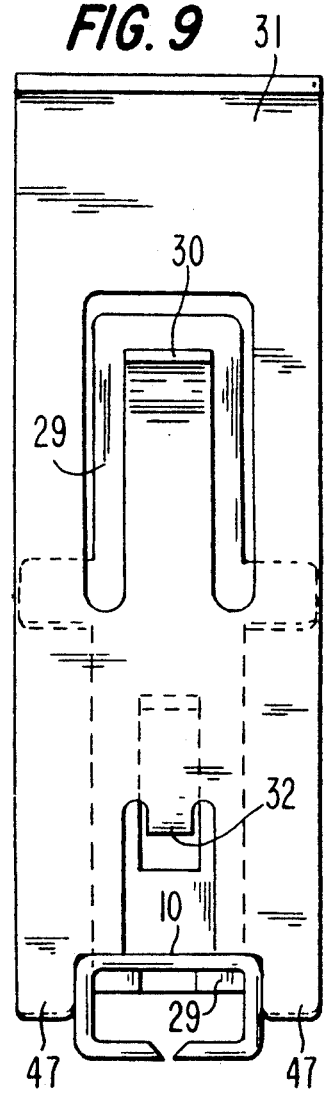
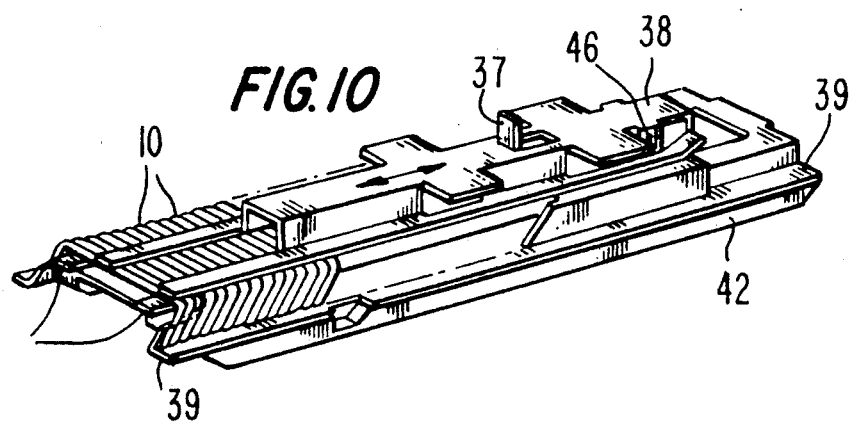

SURGICAL STAPLER

BACKGROUND OF THE INVENTION

This invention relates to a surgical stapler for implanting staples into the skin and/or tissue for wound closure after a traumatic injury or a purposeful incision in a surgical procedure.

It has become a preferred procedure to use staples for wound closure rather than thread or filament sutures. Surgeons choose staples because of the speed with which an incision can be closed as compared with the time consuming placing and tying of thread or filament sutures.

Many surgical staplers have been designed with various features to improve the profile of the stapler to increase visibility for the surgeon during the placing of the staples and to improve the reliability of the stapler with respect to serial delivery of contained staples without jamming. See, for example, U.S. Pat. Nos. 4,014,492, 4,109,844, 4,179,057, 4,202,480, 4,256,251, 4,375,866, 4,407,286, 4,489,875 and 4,527,725. The above patents describe staplers using preformed staples without a forming anvil, staplers having a movable or retractable forming anvil as well as a wide variety of feeding mechanisms to deliver each staple to the delivery point where the staple is deformed during implantation into the skin and/or tissue.

In an effort to improve visibility for the surgeon, the angle formed between the bottom of a stapler and the skin or tissue surfaces being joined has been increased in prior art staplers with the result that it has become increasingly difficult to retain jam-free delivery of the staples, particularly in those staplers where the staples are sorted on a covered retaining track or rail and fed serially thereon to the forming jaws and forming anvil. The increased angle of the stack of staples sorted in such a feeding mechanism of a stapler and the pressure of the biasing means, e.g., a spring biased pusher, tend to cause the stack of staples to buckle and jam the stapler, i.e., a following staple tends to push under a leading staple like a wedge and cause a jam in the feeding mechanism. This problem was at least partially overcome by the teachings of U.S. Pat. No. 4,662,555 which discloses a shuttle in association with the rail as a movable staple retaining cover which moves in the same direction and at the same time as the staples being fed along the rail. This structure provides a reliable surgical stapler in which staples are not likely to jam the staple feed mechanism.

In U.S. Pat. No. 4,662,555 a cantilever spring is disclosed as part of the rail. Its purpose is to support the next staple to be deformed before deformation. A problem has arisen where occasionally the staple will be deformed around the spring 48 which is in the center of the end of the rail. This causes the staple deformed into the tissue to be stuck in the stapler. When the stapler is withdrawn, it tugs at the tissue.

SUMMARY OF THE INVENTION

The surgical stapler of the present invention, preferably in a single use disposable form, comprises a combination of a staple feeding mechanism and a staple forcing mechanism secured in a frame. An actuating trigger is functionally connected to both the staple feeding mechanism and the staple forming mechanism. The staple feeding mechanism includes a rail to guide contained staples serially to a staple forming position. A cantilever spring means is provided as part of the rail for supporting the next staple to be implanted. The spring means is flexible to move out of the path of the next staple as it is deformed. The spring means returns to its rigid position after deformation without interfering with the deformed staples. More particularly, the spring means comprises a pair of spaced apart flexible members which support the web of the staple to be deformed adjacent the legs of the staple at either end of the web. At the onset of deformation of the staple, the ends of the members deflect and then return to their original position with the deformed staple positioned between the members.

The specific advantages of the present surgical stapler will be described and explained more fully in the following detailed description.

BRIEF DESCRIPTION OF THE DRAWING

The surgical stapler of the present invention will be described in more detail with reference to the accompanying drawings which show an illustrative and preferred specific embodiment of the invention.

In the drawings:

FIG. 1 is a perspective view of the surgical stapler of the present invention showing the surgical stapler approximately in the position of use after having implanted surgical staples to close an incision.

FIG. 2 is a side view of the surgical stapler partly in section to show the arrangement of the pawl and pawl pad.

FIG. 3 is a partial view of the stapler showing the attitude of the pawl and pawl spring during the closing movement of the trigger when a staple is being deformed and implanted in tissue.

FIG. 4 is a partial view of the stapler showing the attitude of the pawl and pawl spring at the point of full closure of the trigger (dotted) and during the return movement of the trigger.

FIG. 5 is an enlarged partial view in section of the stapler showing the positions of the various parts when the trigger is in full open position.

FIG. 6 is an enlarged partial view partly in section of the stapler showing the positions of the various parts when the trigger is in the full closed position.

FIG. 7 is a side view in section of the jaw, anvil and staple showing the relationship of these three parts when in position to begin deformation of the staple.

FIG. 8 is a front view partly in section of the jaw, anvil and staple in the same relative positions as in FIG. 7.

FIG. 9 is a front view of the jaw, anvil and staple showing the relationship of these three parts when deformation of the staple has been completed.

FIG. 10 is a perspective view of a combination of the bottom, rail, staples, shuttle and staple pusher.

DETAILED DESCRIPTION OF THE DRAWINGS

Figure 12:
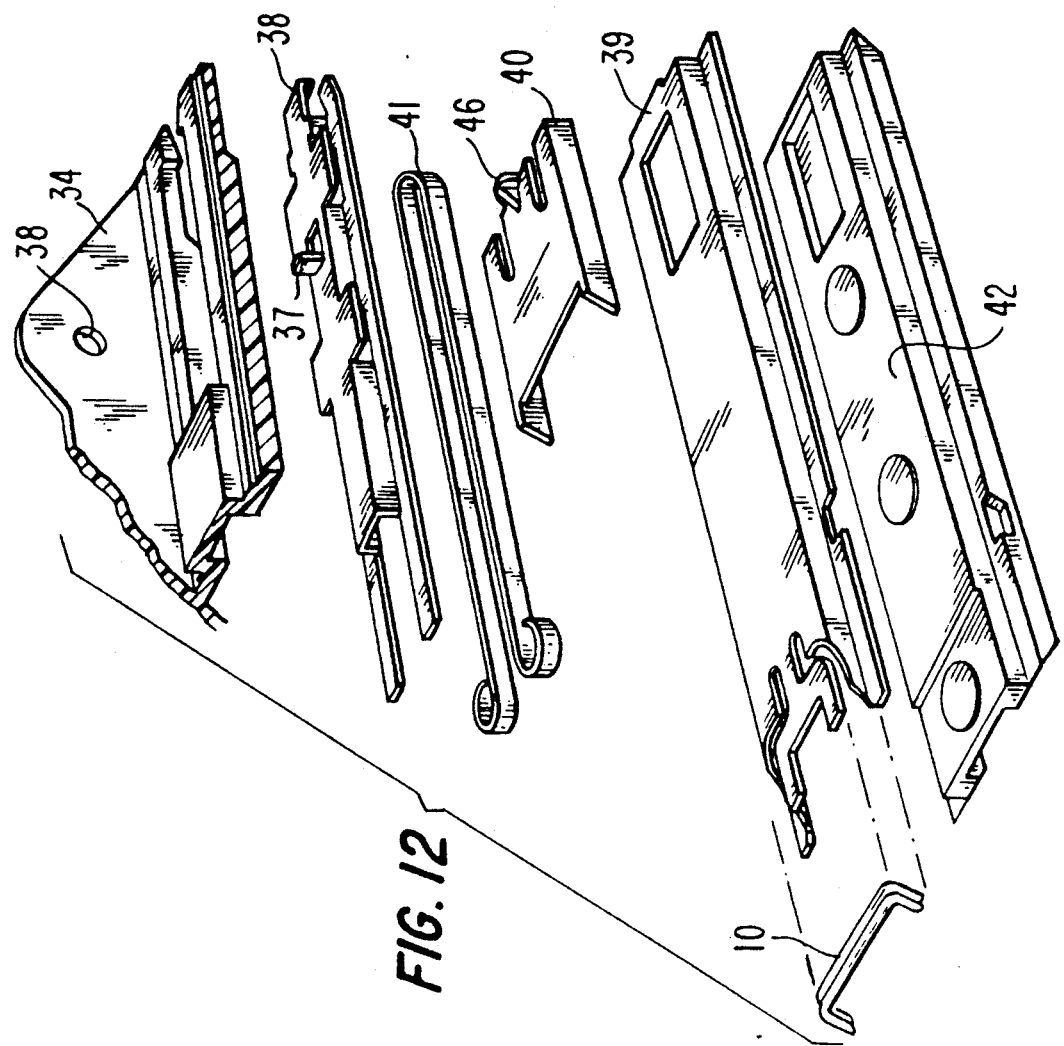
FIG. 12 is a perspective and exploded view of the staple guiding and feeding elements of the stapler.
Figure 11:
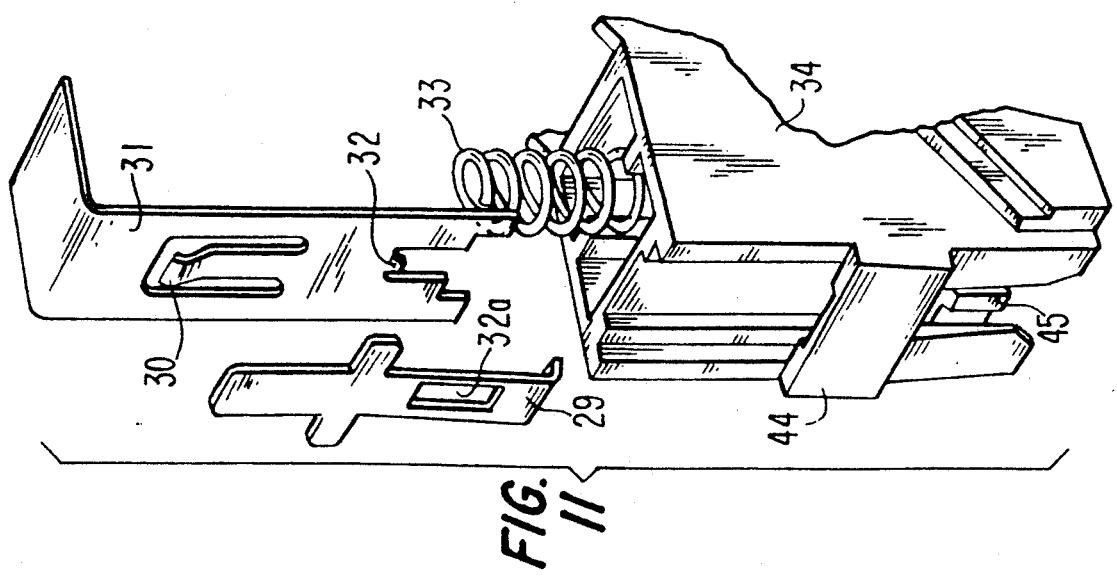
FIG. 11 is a perspective exploded partial view of the anvil, jaw, compression spring and cover block showing the relationship of these parts.

With reference to the accompanying drawings, the same part is identified by the same reference numeral in all figures of the drawings.

In FIG. 1, a specific and preferred embodiment of the surgical stapler of the present invention, indicated generally by reference numeral 20, is shown in an attitude of use after having implanted staples 10 to close an incision 11. The surgical stapler 20 includes a frame 21 and a trigger 22.

FIGS. 2, 3 and 4 show the arrangement of elements to provide for unidirectional movement of the trigger 22 throughout its closing movement as well as throughout its return movement. This is important to prevent malfunction of the stapler either by jamming or by releasing a staple before it is fully deformed and implanted. In FIG. 2, the trigger 22 is in its full open position with respect to the frame 21 and the arrow shows the direction of closing movement. Pawl 23 is shown mounted on trigger 22 by pivot pin 26 and pawl spring 25 is positioned to bias pawl 23 when contacted by either of the ears of pawl 23. Pawl spring 25 is shown as an integrally molded part of trigger 22, but could be a separate leaf spring fastened to trigger 22. Pawl pad 24 is made of a resilient material and may be formed as part of frame 21 or may be a separate part fastened into frame 21 and positioned as shown to be contacted by pawl 23 during the closing movement of trigger 22 as shown in FIG. 3. During this closing movement of the trigger 22, the point of pawl 23 is forced against the resilient pawl pad 24 by the biasing action of pawl spring 25 against an ear of pawl 23. While the pawl 23 is shown as having a single point, it could have multiple points, e.g., a saw tooth configuration, at the point of contact with pawl pad 24. While the closing movement of trigger 22 is in no way hampered by the contact of pawl 23 against pawl pad 24, it is obvious from FIG. 3 that movement in the opposite direction would be prevented by pawl 23 digging into the surface of pawl pad 24. When trigger 22 reaches full closure position as shown in FIG. 4 (dotted), the pawl 23 reaches the step in the pawl pad 24 and turns on pivot pin 26 for the return movement of trigger 22 during which the pawl 23 is biased such that no closing movement is possible until the return movement is completed.

FIG. 5 shows the relative positions of the parts of the staple feeding assembly and the staple forming assembly when the trigger 22 is in the full open position and FIG. 6 shows the relative positions of the same parts when the trigger 22 is in the full closed position. As shown, the frame 21 provides a biasing spring 28 as an integral part of frame 21, but this could be provided by a separate leaf spring or the like fastened to frame 21. The biasing spring 28 biases the moving anvil 29 out of the path of staples 10 as shown in FIG. 5. When the trigger 22 is moved to the full closed position as in FIG. 6, the cam surface 30 of the staple forming jaw 31 tilts the moving anvil 29, which is non-planar, i.e., is a combination of two planar sections, about the fulcrum formed by the intersection of the two planes to position the forming end of the anvil 29 into the path of the staples 10. When the trigger 22 is again moved to the full open position (FIG. 5), the cam surface 32 on the staple forming jaw 31 assists the biasing spring 28 in tilting the moving anvil 29 out of the path of staples 10. A window 32a in the anvil 29 is positioned opposite the cam surface 32 when the anvil 29 is under the influence of cam surface 30.

The frame 21 includes an open window 43 which together with strap 44 on the cover block 34 serves to locate the cover block 34 within the frame 21 during assembly. The frame 21 has a cut out 46 at the the tip to match a similar contour of the cover block 34 and provide clearance for the moving anvil 29. The frame 21 is preferably molded from plastic, e.g., a clear or pigmented polycarbonate, particularly when the surgical stapler 20 is made as a single use disposable device.

The trigger 22 rotates around the pivot pin 27 within the frame 21. The nose 22a of the trigger 22 bears on the top of staple forming jaw 31, and compression spring 33, positioned in a well in cover block 34, biases jaw 31 to the upward or withdrawn position and thereby the trigger 22 to the full open position (FIG. 5).

Cover block 34 provides a base for assembling the individual elements that make up the staple feeding mechanism and the staple forming and implantation mechanism. As shown in FIGS. 5, 6, 11 and 12, the cover block 34 includes contours into which fit the staple forming jaw 31 and forming anvil 29, both of which are retained in place by strap 44. Cover block 34 also provides a well to position compression spring 33 for biasing forming jaw 31 and the trigger 22. The staple deforming legs 47 of the jaw 31 are part of the single piece jaw 31 and are shaped to force the staple 10 around the forming anvil 29 (as shown in FIGS. 8 and 9) in the final closing movement of the trigger 22. The staple feeding mechanism (see FIGS. 10 and 12) composed of the shuttle 38, pusher 40, saddle spring 41, rail 39 and bottom 42 is assembled in combination with cover block 34. The flexible members 120 and 122 are provided as part of rail 39 for retention of the next staple to be deformed prior to the movement into place of the forming end of anvil 29. Cover block 34 includes as an integral part the staple stripper block 45 which prevents any tendency of a formed staple 10 being drawn into the stapler 20.

The cover block 34 provides a pair of holes 38 (see FIG. 12) which function as bearings for the pivot pin 27 about which the trigger 22 rotates. The hub 35 of the trigger 22 is provided with a keyway 36 to accommodate a tang 37 of shuttle 38. The keyway 36 and tang 37 cooperate to impart linear motion to the shuttle 38 from the rotary motion of the trigger 22. During the closing motion of the trigger 22, the hub 35 (as seen in FIGS. 5 and 6) rotates counterclockwise and consequently the keyway 36 moves the tang 37 and the shuttle 38 toward the rear of the surgical stapler 20. In this same part of the cycle of operation of the stapler, i.e., the closing of the trigger 22, the anvil 29 is tilted into the path of the next staple 10 to be dispensed and then the jaw 31 which is moving downward contacts and forms the staple 10 around the anvil 29 as the staple 10 is implanted. While the trigger 22 is closing, the staples 10 on the rail 39 do not move, i.e., they do not advance toward the front of the stapler 20. Such advance of the staples 10 takes place only during the return or opening movement of the trigger 22 and then only after the jaw 31 has been retracted sufficiently to cause the anvil 29 to tilt out of the way and release the implanted staple 10. When this release takes place, the pusher 40 under the influence of saddle spring 41, which is connected to the pusher ear 46, moves the row of staples 10 on rail 39 a distance equal to the thickness of a staple 10 so that the next staple 10 is placed in position to be formed and implanted. Throughout this return or opening movement of the trigger 22, the hub 35 (as seen in FIGS. 5 and 6) rotates clockwise and consequently the keyway 36 moves the tang 37 and the shuttle 38 toward the front of the surgical stapler 20. Therefore, during that part of the return or opening movement of the trigger 22 that the staples 10 are being moved on rail 39 by pusher 40, the shuttle 38 is constantly moving in the same direction as the staples 10. For this reason, the staples 10 are less like to jam because friction between the crowns of the staples 10 and the retaining cover member, i.e., the shuttle 38, has been eliminated. In addition, the motion of the shuttle 38 assists the pusher 40 in uniform movement of staples 10.

Figure 13A:
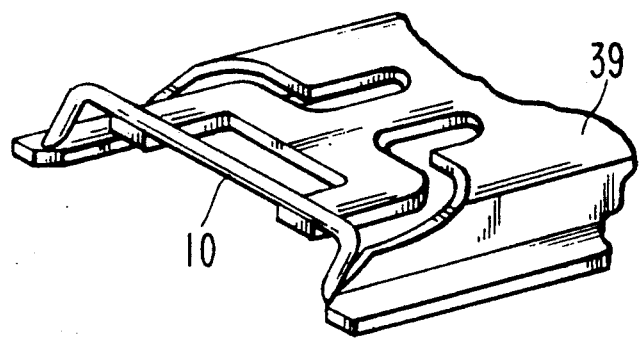
FIGS. 13A through 13C are enlarged views of a portion of the rail shown in relation to the next staple to be deformed during various stages of deformation of the staple.
Figure 13B:
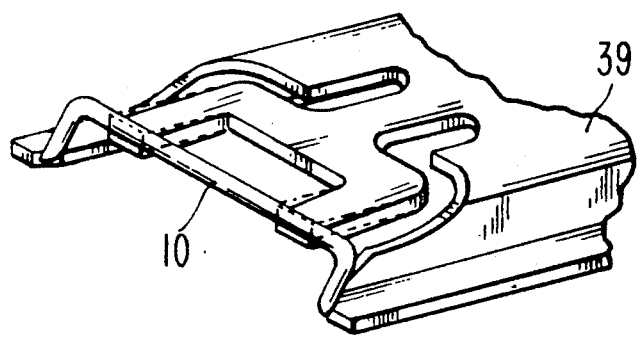
Figure 13C:
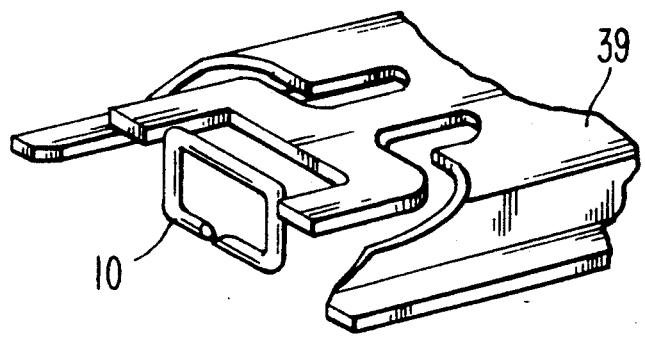

Referring now to FIGS. 13A through 13C, an enlarged view of the end of the rail 39 nearest the staple implantation site is shown. The rail 39 for most of its length comprises a flat planar elongated surface 102 with opposite sides 104 extending downwardly from the surface 102 along surface 102 longitudinal edges. A ledge 106 extends outwardly from the bottom of the sides 104. The rail is adapted to support a plurality of staples 10, each staple comprising a web 108 and two legs 110 extending substantially perpendicularly from the ends of the web 108. The width of the surface 102 is a little less than the length of the web of the staple so that the legs of the staple extend down along the sides 104. The legs are disposed at an angle along the sides 104 as shown in FIG. 10.

At the distal end of the rail 39, nearest the implantation site, the rail comprises a pair of spaced apart flexible members 120 and 122 which are free to flex up and down at their free ends and connected at their opposite ends to a base portion 124 which in turn is connected by arm 126 to the surface 102 of the rail. The arm 126 is formed by slots 128 extending into the surface 102.

Figure 14:
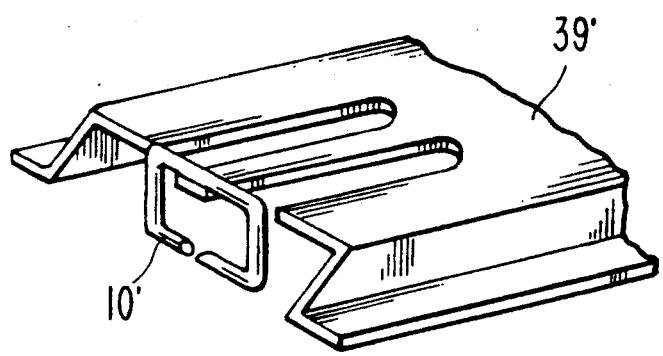
FIG. 14 is an exploded view of a similar portion of a prior art rail shown in relation to a fully deformed staple.

When the deforming legs 47 of the jaws 31 are in the position shown in FIG. 8 just prior to deformation of the staple, the staple to be deformed is supported by the free ends of the members 120 and 122 as shown in FIG. 13A. As the staple is pressed down onto the anvil 29 the members 120 and 122 deflect downwardly out of the staple path so that the web of the staple contacts the anvil. See FIG. 13B where the dotted line shows the original position of the members 120 and 122. The members 120 and 122 are shown deflected in FIG. 13B. Closing of the anvil or other parts of the instrument are not shown in FIGS. 13A through 13C. FIG. 13C shows the staple fully formed and positioned between the members 120 and 122. See also FIG. 6. Once the web is pushed past the deflected members 120 and 122 and bent about the anvil 29, the members return to their original position. No contact between the members 120 and 122 and the formed staple is possible, eliminating the sticking of the staple to the instrument. FIG. 14 shows how it is possible with the prior art rail 39' having a cantilever spring 48', which is located in the center of the rail, for the formed staple 10' to be stuck on the spring 48'.

As disclosed above, the anvil 29 will move out of the staple path as the trigger 22 returns to its open position and the staple deformed into the tissue is totally clear of the instrument.

The frame 21, trigger 22, pawl pad 24, cover block 34, pusher 40 and bottom 42 may all be molded of plastic, e.g., a clear or pigmented polycarbonate, particularly for a single use disposable stapler. However, the pawl 23, anvil 29, jaws 31, shuttle 38, rail 39 including members 120 and 122 as well as the compression spring 33 and the saddle spring 41 are preferably made of stainless steel.

While the surgical stapler of the present invention could be made as a reuseable device by providing for the reloading of staples after the initial supply has been exhausted, it is preferred to provide the stapler as a single use disposable device. Consequently, some of the parts described in the detailed description have been designed knowing that reloading is not intended.

If desired, the surgical stapler described could be modified to make disassembly and reloading of staples possible. It is believed that such modifications do not require specific description because they would be obvious to a designer skilled in this art. For example, in the disposable form of the surgical stapler 20 of this invention, the pivot pin 27 does not pass through either side of the frame 21 but is held in place in the trigger 22, hub 35 and cover block 34 holes 38 by the inside surfaces of the frame 21 with the cover block 34 assembly cemented into the frame 21. In a reusable version, the pivot pin 27 could pass through the sides of frame 21 and be held in place by suitable means so that the cover block 34 assembly would be retained within frame 21 without cementing and could be removed for reloading with a new supply of staples 10 or replaced with a preloaded cover block 34 assembly as a cartridge.

What I claim is:

1. In a surgical stapler comprising means to deliver a surgical staple having a web and a pair of tissue penetrating legs extending substantially perpendicularly from either end of said web to a site of implantation and means to actuate deformation means to deform the staple into a tissue retaining configuration at the site of implantation wherein the staple delivery means includes a rail to guide the travel of the staples, a biasing means to move the staples along the rail, and a retaining means to retain the staples on the rail, the improvement which comprises a cantilever spring means which forms part of the end of the rail at the site of implantation for supporting the next staple to be implanted before deformation and for not supporting same after it has been deformed, said spring means being flexible to move from its original position to allow said next staple to be deformed and return to its original position after deformation without interference with said deformed next staple.

2. The surgical stapler of claim 1 wherein said spring means comprises at least a pair of spaced apart flexible members which support the web of said next staple adjacent said legs so that said next staple is positioned between said members after it is deformed.

3. The surgical stapler of claim 2 wherein said deformation means comprises a movable anvil disposed to tilt out of the staple path after said next staple is formed.

4. The surgical stapler of claim 3 wherein the ends of said members are bent out of the path of said next staple during the onset of deformation.

* * * * *